(12) United States Patent
Bryant et al.

(10) Patent No.: US 6,335,625 B1
(45) Date of Patent: Jan. 1, 2002

(54) PROGRAMMABLE ACTIVE MICROWAVE ULTRAFINE RESONANCE SPECTROMETER (PAMURS) METHOD AND SYSTEMS

(76) Inventors: Paul Bryant, 824 College Pkwy., Rockville, MD (US) 20850-1931; Martin Silverstein, 7041 N. Correida de Venado, Tucson, AZ (US) 85718; Larry W. Fullerton, 120 Wibledon Rd., Brownsboro, AL (US) 35741

( * ) Notice: Subject to any disclaimer, the term of this patent is extended or adjusted under 35 U.S.C. 154(b) by 0 days.

(21) Appl. No.: 09/507,346

(22) Filed: Feb. 18, 2000

Related U.S. Application Data (60) Provisional application No. 60/121,039, filed on Feb. 22, 1999.

(51) Int. Cl.[7] .............................. G01R 27/04; G01V 3/00
(52) U.S. Cl. ........................................ 324/637; 324/316
(58) Field of Search ....................................... 324/318, 633, 324/637, 639, 641, 361, 316

(56) References Cited

U.S. PATENT DOCUMENTS

| | | | | |
|---|---|---|---|---|
| 5,489,848 A | * | 2/1996 | Furukawa | 324/318 |
| 5,592,086 A | * | 1/1997 | Weinstock et al. | 324/318 |

* cited by examiner

*Primary Examiner*—Glenn W. Brown
*Assistant Examiner*—J Kerveros (57) ABSTRACT

A preferred embodiment of the present invention includes a system for detecting a presence of a macromolecule having one or more resonant frequencies. The system includes a pulse generator (a T-wave generator in the most preferred embodiment) for generating a detection profile having a detection set of T-waves and applying the detection profile to a sample including the macromolecule, at least one T-wave having a center frequency substantially centered on one of the resonant frequencies of the macromolecule, a detector for receiving the detection profile after the application of the detection profile to the sample, an analyzer, coupled to the detector, for determining a T-wave absorption profile by identifying which T-waves of the set of T-waves have been wholly or partially absorbed by the sample and to subsequently identify the macromolecule by use of the absorption profile.

16 Claims, 5 Drawing Sheets

FIG_1

FIG_2

Fig_3

Fig_4

Fig_5

PROGRAMMABLE ACTIVE MICROWAVE ULTRAFINE RESONANCE SPECTROMETER (PAMURS) METHOD AND SYSTEMS

CROSS-REFERENCES TO RELATED APPLICATIONS

This application is a non-provisional filing from Ser. No. 60/121,039, filed Feb. 22, 1999, the disclosure of which is incorporated herein by reference for all purposes.

BACKGROUND OF THE INVENTION

The invention relates generally to the real time detection and identification of chemical or biological macromolecules via non-destructive testing, and more specifically to a programmable active microwave (GHz to THz in the most preferred embodiment) ultrafine resonance spectrometry system, apparatus and method.

There exists a great need for a remote sensing system capable of macromolecule substance detection and identification. As used herein, the term macromolecule means a large molecule like a polymer, for example, made up of many (a few to millions) of repeating subunits. A definition for a macromolecule from physical chemistry includes a molecule that has molecular motion of two types: intramolecular modes ("optical photons") and lattice vibration ("acoustic phonons"). The intramolecular modes are low frequency torsions, ring puckering and hindered rotations generally present in the gas phase but modified by the solid state environment. The term macromolecules includes both complex inorganic (e.g., nitrogen-based explosives) and long-chained DNA polymers. The prior art includes spectrometer systems, high-energy cross-section absorption systems, and polymerase chain reaction systems that are used for the detection and identification of macromolecules.

Prior art spectrometer systems are based on quantum mechanics, and application of statistical sampling theory to identify macromolecules. These systems query a large sample space, are likely to contain undesired materials which act as interferents and contaminants, collectively used herein as foreign bodies. An interferent typically exists separate from the macromolecule and may interfere with spectroscopic measurement through absorption and attenuation of incident measuring radiation. A contaminant may be attached or otherwise reactively associated with a macromolecule and may interfere with spectroscopic measurement through its absorption and attenuation of incident measuring radiation or through altering the response characteristics of the associated macromolecule.

Many prior art systems take large numbers of samples to amplify any signal. Mass spectrometers may require days of sample acquisitions to achieve the required integration.

High-energy cross-section absorption systems are also based upon quantum mechanics and require long integration times. Moreover, they use a single spectrum query. Several macromolecule species may contain the same unique spectral absorption (e.g., packed wool and explosives).

Polymerase chain reaction systems rely on statistical sampling of antigen interactions, and consequently may take minutes to hours before threshold detection levels are achieved. Furthermore, these systems require special handling, may easily be contaminated, and are expensive to build and maintain.

As an example of a specific prior art system, none of the existing methods for the remote detection of hidden illicit drugs and drug-containing plants is completely adequate. Techniques based on the detection of vapors, both of drugs and the precursor processing chemicals are not sensitive to drugs, because drugs generally have a negligible vapor pressure at room temperature. X-ray techniques are not very selective for drugs, as they penetrate without absorption or reflection.

SUMMARY OF THE INVENTION

The preferred embodiment of the present invention provides a programmable active microwave (GHz to THz) ultrafine resonance spectrometer (PAMURS) instrument. The systems described herein may be used to cover frequencies from the far infrared to the deep ultraviolet, about $1 \times 10^{12}$ Hz to about $3 \times 10^{16}$ Hz, the range from microwaves to X-rays. This PAMURS instrument overcomes the limitations of the prior art macromolecule detection, identification and disruption/elimination systems.

Some key advantages derive from the characterization of such a PAMURS instrument as a real-time system. The PAMURS instrument, in a preferred embodiment, combines several operational modes, such as initialization in a broadband search mode (e.g. any DNA detected), which may be subsequently switched to a narrowband mode for specific identification of one or more types of macromolecules. When a macromolecule is detected, the PAMURS instrument is able to rapidly progress through a library search to narrow down and specifically identify the detected material. The preferred embodiment of the PAMURS instrument is highly accurate due to use of multiple frequencies to create a 'notch filter' for recognizing a macromolecule resonating at only the selected group of frequencies. As the number and precision of the applied frequencies increases, it becomes less likely for two different macromolecules to be identified as the same macromolecule.

The PAMURS instrument uses absorption spectra and emission spectra for detection and identification. Two distinct macromolecules having the same absorption spectra are unlikely to have identical emission spectra, as the decay function is related to the macromolecule' electric field and its mass. This is particularly true as catalogs of 'signature' spectra for the various macromolecules of interest are developed. These catalogs make the PAMURS instrument adaptable, as new frequency sets may be uploaded to the instrument library as required or desired.

The PAMURS instrument is able to screen out interferents and contaminants (particularly water vapor and ozone absorption) due to use of the narrow band spectra chosen and the use of a multiple beam approach. The PAMURS instrument is able to detect and identify very low thresholds of macromolecules (on the order of parts per billion) because it is a radio frequency (RF) based instrument. RF based systems have inherent high signal-to-noise, with consequent low error rates. Further, the likelihood of false positive detection is low. For these reasons, a PAMURS instrument may be a remote sensing imaging system because the ozone and water vapor absorption bands in the THz ranges may be avoided by the narrow RF bandwidths. In another preferred embodiment, a PAMURS instrument may be an inhaler/sampler for airborne and waterborne applications.

The PAMURS instrument has a direct relationship between the power employed by the system, and the rate and distance of the detection. By increasing the power of the PAMURS instrument, the detection rate increases for both aerosols and surface materials, and the detectable distance of the macromolecules from the sensor increases as well.

The narrow signals used by the PAMURS instrument decreases the risk of interference with other RF signals. The exposure risk to humans from irradiation is minimal due to the frequencies and the low power levels used.

Theoretical predictions for a PAMURS instrument indicate that it should have minimal Type II Errors as resonance signal returns are similar to those that would be that transmitted (i.e., there should be no unexpected signal returns) unless an unexpected Doppler shift occurs.

A preferred embodiment of the present invention includes a system for detecting a presence of a macromolecule having one or more resonant frequencies. The system includes a pulse generator (a T-wave generator in the most preferred embodiment) for generating a detection profile having a detection set of T-waves and applying the detection profile to a sample including the macromolecule, at least one T-wave having a center frequency substantially centered on one of the resonant frequencies of the macromolecule, a detector for receiving the detection profile after the application of said detection profile to said sample, an analyzer, coupled to the detector, for determining a T-wave absorption profile by identifying which T-waves of the set of T-waves have been wholly or partially absorbed by the sample and to subsequently identify the macromolecule by use of the absorption profile.

Another preferred embodiment of the present invention includes a system for detecting a presence of a macromolecule having one or more resonant frequencies. The system includes a T-wave generator for generating a detection profile having a detection set of T-waves and applying the detection profile to a sample including the macromolecule, at least one T-wave having a center frequency substantially centered on one of the resonant frequencies of the macromolecule, the resonant frequency inducing the macromolecule to reradiate an emission profile including a set of emission frequencies different from frequencies of the set of T-waves, a detector for receiving the emission profile after the application of the detection profile to the sample; and an analyzer, coupled to the detector, for determining a T-wave absorption profile by identifying which T-waves of the set of T-waves have been wholly or partially absorbed by the sample as derived from the emission profile and to subsequently identify the macromolecule.

Reference to the remaining portions of the specification, including the drawing and claims, will realize other features and advantages of the present invention. Further features and advantages of the present invention, as well as the structure and operation of various embodiments of the present invention, are described in detail below with respect to accompanying drawing. In the drawing, like reference numbers indicate identical or functionally similar elements.

DESCRIPTION OF THE SPECIFIC EMBODIMENTS

Table of Contents

I. Overview
II. Structure
   A. Absorption Detection Mode
   B. Remote Detection Mode
III. Operation
   A. Absorption Detection Mode
   B. Remote Detection Mode
IV. Preferred Embodiments for Pulse Generators
V. Conclusion
I. Overview Spectroscopy in the electromagnetic spectrum of far infrared to deep ultraviolet (i.e., the spectrum from microwaves to X-rays) offers the possibility of molecule-specific detection of many different macromolecules, such as illicit drugs and drug-containing plants such as coca or poppy, DNA, hazardous materials (biological and chemical) that are airborne or deposited, aerosol products of human stress (i.e., buried-alive victims), explosives, weed and disease pathogens, and processing chemicals needed to transform material into illegal products, for example.

The submillimeter wave and Terahertz region of the electromagnetic spectrum is traditionally called the far infrared region (30–300 cm-1)The absorption of radiation in this region by solids is associated with molecular motion of two types: intramolecular modes ("optical phonons") and lattice vibrations ("acoustic phonons"). The intramolecular modes are low frequency torsions, ring puckering and hindered rotations generally present in the gas phase but modified by the solid state environment. It is these modes that offer the possibility of selective detection of macromolecules and compounds and compositions of macromolecules.

For each macromolecule or compound it is possible to find unique chemical groups that will usually have a signature in the far infrared to deep ultraviolet spectrum. The uniqueness is guaranteed by the fact that the target will have a unique mass-momentum coefficient. Any chemical that is unique will have a set arrangement of linked atoms that will generate a class of mass-momentum coefficients. The more complex the molecule, the greater the number of mass-momentum coefficients that will exist. When folding and other spatial arrangements are taken into account, the number of coefficients again increases. Each mass-momentum coefficient will translate into a set of resonant frequencies. The problem will not be finding resonances in the frequency range desired, but assuring that the resonance will not be duplicated in another, different molecule. As more molecules are analyzed and described to develop detection libraries, finding non-duplicative resonances will become easier. In the short term, some implementations may use standard spectroscopy against likely backgrounds to assure that the unique signature of a molecule has been found. In the most preferred embodiment, three separate unique resonances will provide a sufficient guarantee that the desired molecule is present. For other implementations, a single unique resonance may be all that is necessary, while in other cases two would be desirable, or four or more resonances.

The preferred PAMURS resonance system has at least two criteria. The first criterion is that the form of the wave applied to the sample should not be strictly sinusoidal. Instead it is preferably a spiked wave, also commonly called a pulsed wave. Most preferably, the pulsed waves used herein are in the TeraHertz range and are referred to as T-waves. T-waves are well known in the prior. In general, T-waves may be generated and used in either the time domain (generated by ultrashort short laser pulses) or in the frequency domain (generated by mixing continuous or quasi-continuous electromagnetic radiation). For the former case one paper would be "T-Ray Imaging" by D. M. Mittleman, R. H. Jacobsen and M. C. Nuss in IEEE Journal of Selected Topics in Quantum Electronics, vol. 2, pg. 679 (1996), for the latter case a good review is "Tunable Far Infrared Spectrometers" by G. A. Blake et al. Review of Scientific Instruments, 62, 1693 (1991), both hereby expressly incorporated by reference for all purposes.

Sinusoidal waves are absorbed and are re-radiated by non-target molecules, commonly called interferents or contaminants (collectively "foreign bodies"). Frequently, these foreign bodies absorb at one energy level and re-radiate at several levels. This re-radiation broadens the initial wave, and prevents it from penetrating to any useful depth in the background, or returning any useful information. T-waves have extremely narrow bases, in the order of picoseconds. Only when the interferent has the exact same resonant frequency as the target molecule will it be able to absorb the T-wave.

The second criterion is that the center of the T-wave peaks should be almost exactly at the targeted resonant frequency. The deviation from the exact frequency is preferably less than half the base of the T-wave. When these two criteria are met, and the requisite number of unique signature frequencies (three in the preferred embodiment) are known for the target molecule, then detection of the molecule, if it is present, should be accomplished.

The type of detection described above requires that the macromolecule under test to be located between a radiator antenna and a detector antenna. This first type of detection is referred to herein as an absorption detection mode. There is another mode, referred to as a remote detection mode, in which the sample to be analyzed is not positioned between the antennae. It is possible, in this remote detection mode, for the radiator antenna and the detection antennae to be located at the same location, actually physically side-by-side. A third criterion exists for this remote detection mode. The unique resonant frequency must be one where the molecule absorbs at the radiated frequency and re-radiates at two or more longer wavelength frequencies some significant portion of the time. One additional benefit of using this type of resonant frequency is the target molecule will re-radiate only at certain frequencies. If other molecules absorb the resonant frequency, they will radiate at different frequencies, due to their difference in mass-momentum coefficients. The detector antenna is optimized for the correct longer wavelength frequencies.

II. Structure

The PAMURS instrument, as indicated above, includes two operational configurations: an absorption detection mode and a remote detection mode. In the preferred embodiment, the configuration of the PAMURS instrument in either configuration includes a programmable pulse generator (T-wave generator in the preferred embodiment), a detector and an analyzer. The T-wave generator forms a desired detection profile having a set of T-waves. There may, depending upon the application, be one or more different base frequencies for the T-waves in the detection profile. The specific frequencies chosen for the detection profile are dependent upon the macromolecule or group of macromolecules to be detected, identified, and/or disrupted. Preferably, the base frequencies are chosen to match unique resonant frequencies of the macromolecule(s) to be detected. Many candidate frequencies may be included within the detection profile, depending upon the degree of uncertainty of the unknown macromolecules and the range over which possible macromolecules are to be detected and identified. Further, the chosen frequencies are designed to avoid the attenuating and altering affects of foreign bodies (e.g., interferents and contaminants).

In some applications, it is not necessary that all frequencies correspond to unique resonance frequencies of the macromolecule, as long as the entire detection profile defines the macromolecule as uniquely as desired. In other words, there may be some applications for which it will be sufficient to identify the macromolecule as a class of macromolecule, and specific distinction among the class is not necessary. For example, it may be desirable to determine whether any form of DNA is present, not a specific type of DNA.

The detector receives radiation after the detection profile has interacted with the sample containing the macromolecule(s) under test. The detector will have a different structure, depending upon whether the PAMURS instrument is configured for absorption detection mode or for remote detection mode. In the case where the PAMURS instrument is used to disrupt the specific macromolecule, no detector is necessary unless it is desirable to ascertain whether the macromolecule has been eliminated or the quantity sufficiently reduced from the sample.

In the absorption detection mode, the detector receives signals from the detection profile that have not been sufficiently attenuated by the sample. The radiation incident on the detector is dependent upon the operational mode, the number of different frequencies in the detection profile and the different macromolecules in the sample. The PAMURS instrument is configurable to operate iteratively, with successive detection profiles chosen specifically to confirm, rule out, or classify, groups, sub-groups, or specific macromolecules.

Many of the preferred embodiments of the PAMURS instruments also include an analyzer for determining a T-wave absorption profile. The absorption profile identifies which T-waves of the set of T-waves have been wholly or partially absorbed by the sample. The absorption profile is used to identify the desired characteristic(s) of the sample based upon the detection profile and any characteristics previously established for the sample.

A. Absorption Detection Mode

Figure 1:
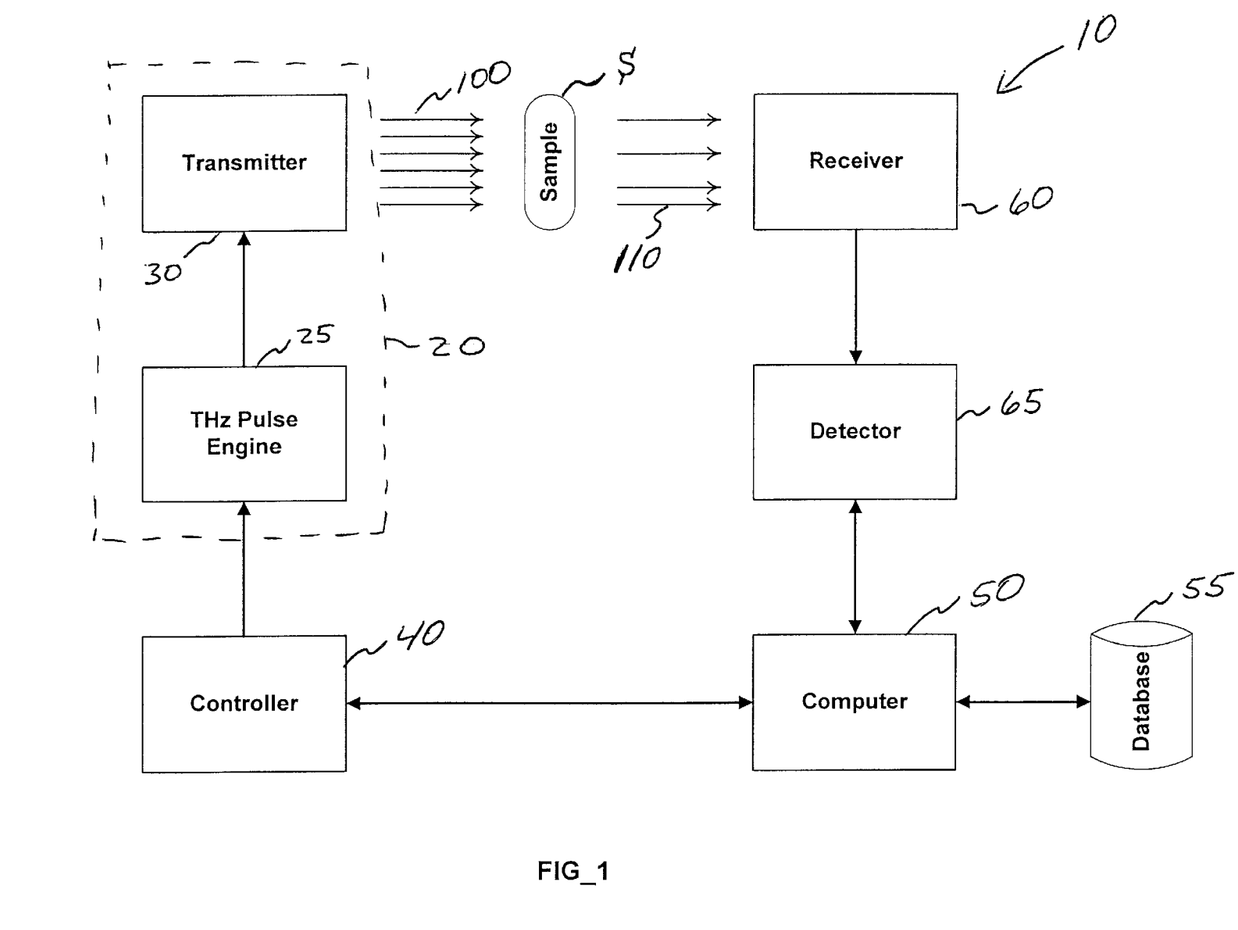
FIG. 1 is a block diagram of a preferred embodiment of a PAMURS instrument configured for operation in an absorption detection mode.

FIG. 1 is a block diagram of a preferred embodiment of a PAMURS instrument 10 configured for operation in an absorption detection mode. PAMURS instrument 10 includes a pulse generator (e.g., a T-wave generator) 20 (including in this preferred embodiment a TeraHertz pulse engine 25 and a transmitter 30), a controller 40, a general purpose programmable computer 50 coupled to a database 55, a receiver 60 and a detector 65. PAMURS instrument 10 may detect, identify or disrupt one or more macromolecules in a sample S.

T-wave generator 20 may be implemented in any of several ways, depending upon the desired base frequency or frequencies it is to generate. In any embodiment, T-wave generator 20, responsive to control signals from controller 40, generates a detection profile 100 having one or more T-waves of specific base frequency. The frequency or frequencies of the detection profile are chosen to substantially match at least one possible resonance frequency of one or more macromolecules that may be included in sample S.

TeraHertz pulse engine 25 produces T-waves of the desired frequency wave and having the requisite characteristics. Transmitter 30, responsive to the output of TeraHertz pulse engine 25, composes and transmits detection profile 100. Transmitter 30 directs detection profile 100 to be incident upon sample S. The specific structure of transmitter 30 is dependent upon the frequency and nature of the T-waves to be generated. In some embodiments, it may include an antenna (not shown) for radio-frequency transmissions. In other embodiments, the T-waves may be embodied in a visible portion of the electromagnetic spectrum, requiring a different form of transmitter. The construction and integration of a suitable transmitter 30, once the desired frequency range for the detection profile is known, is within the skill of a person of ordinary skill. The requirements are to compose and direct the set of T-waves into detection profile 100 and direct detection profile 100 to be incident on sample S.

Controller 40 is responsive to control signals provided from computer 50. The control signals indicate a set of T-waves to be produced by T-wave generator 20, and controller 40 interacts with T-wave generator 20 to cause T-wave generator 20 to compose and issue the proper detection profile 100.

Computer 50, in the preferred embodiment, is a general purpose programmable computer including a display, I/O (keyboard, pointing device(s), voice recognition subsystems), a central processing unit, volatile and non-volatile memory, including fixed and portable media (e.g., floppy or zip disks), for storing sequences of instructions to operate in conjunction with the central processing unit and to control PAMURS instrument 10, and to analyze data from detector 60 as will be described further below. Additionally, computer 50 interacts in a well-known fashion with database 55. Computer 50 communicates with controller 40 and detector 60 in any of a number of ways, depending upon a particular application. In some cases, controller 40, computer 50, and database 55 may be integrated into a single device. In other cases, one or more components may be located remote from the other or others. In such cases, the components may communicate with each other through hard-wire connection including fiber optic, network or Internet connections, or through wireless communications channels.

Database 55 includes libraries of signature resonance frequencies for various macromolecules and foreign bodies (i.e., interferents and contaminants). Either stored directly, or derived from the data stored in database 55, computer 50 establishes the desired detection profile 100 to be transmitted from T-wave generator 20. Database 55 may be locally or remotely updated as new signature resonance frequencies or detection profiles are established and verified.

Receiver 65 receives a T-wave absorption profile 110 which is the frequency profile that results from interaction of detection profile 100 with sample S. Sample S, depending upon the macromolecule and foreign body composition, will interact with detection profile 100 to attenuate, broaden or eliminate certain frequencies of the set of incident T-waves to produce T-wave absorption profile 110. Receiver 65 passes T-wave absorption profile 110 on to detector 60 for analysis, and is constructed dependent upon the nature of the frequencies of the transmitted T-waves.

Detector 60, in the preferred embodiment, determines the existence and attenuation level of the radiation in T-wave absorption profile 110. In some instances, detector 60 checks only each T-wave base frequency included in detection profile 100. In other instances, it may additionally check for evidence of interaction of detection profile 100 and a foreign body between transmitter 30 and receiver 65 by checking for the existence of frequencies not included in detection profile 100.

Detector 60, in conjunction with computer 50, analyzes absorption profile 110 and compares it to detection profile 100 and to data in database 55 to establish desired information about sample S. Depending upon the operational mode or the degree of specificity to which macromolecules in sample S are to be detected or identified, one or more iterations may be necessary.

B. Remote Detection Mode

Figure 2:
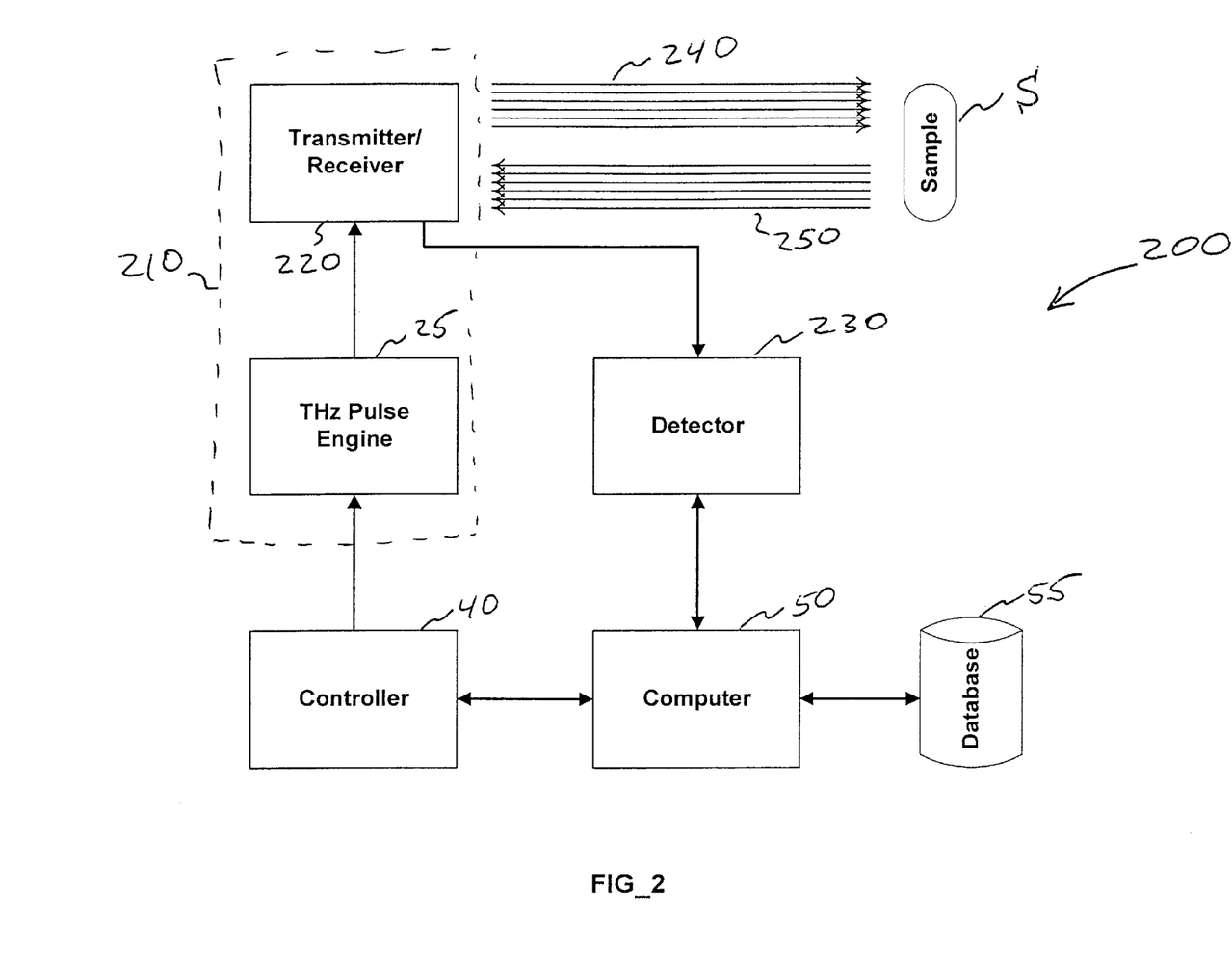
FIG. 2 is a block diagram of a preferred embodiment of a PAMURS instrument configured for operation in remote detection mode.

FIG. 2 is a block diagram of a preferred embodiment of a PAMURS instrument 200 configured for operation in remote detection mode. The structure of PAMURS instrument 200 is similar to PAMURS instrument 10 described above and shown in FIG. 2, while including the following differences.

PAMURS instrument 200 includes a pulse generator 210 (including in the preferred embodiment a TeraHertz pulse engine 25 and a transceiver 220), a controller 40, a general purpose programmable computer 50 coupled to a database 55, and a detector 230. PAMURS instrument 200 may detect, identify or disrupt one or more macromolecules in a sample S. To simplify the following discussion, pulse generator 210 will be described as producing T-waves. It is understood that other pulses and frequencies within the applicable range may be used and produced, other than teraHertz waves, without departing from the spirit and scope of the present invention.

Pulse generator 210 may be implemented in any of several ways, depending upon the desired base frequency or frequencies it is to generate. In any embodiment, Pulse generator 210, responsive to control signals from controller 40, generates a detection profile 240 having one or more T-waves of specific base frequency. The frequency or frequencies of the detection profile are chosen to substantially match at least one possible reactive resonance frequency of one or more macromolecules that may be included in sample S. A reactive resonance frequency is a frequency at which a macromolecule will respond by absorbing some of the incident energy and re-radiating at one or more specific frequencies a significant portion of time and at a sufficient amplitude.

TeraHertz pulse engine 25 produces T-waves of the desired frequency wave and having the requisite characteristics. Transceiver 220, responsive to the output of TeraHertz pulse engine 25, composes and transmits detection profile 240. Transceiver 220 directs detection profile 240 to be incident upon sample S. The specific structure of transceiver 220 is dependent upon the frequency and nature of the T-waves to be generated. In some embodiments, it may include an antenna (not shown) for radio-frequency transmissions. In other embodiments, the T-waves may be embodied in a visible portion of the electromagnetic spectrum, requiring a different form of transmitter. The construction and integration of a suitable transceiver 220, once the desired frequency range for the detection profile is known, is within the skill of a person of ordinary skill. The requirements are to compose and direct the set of T-waves into detection profile 240 and direct detection profile 240 to be incident on sample S.

Controller 40 is responsive to control signals provided from computer 50. The control signals indicate a set of T-waves to be produced by pulse generator 210, and controller 40 interacts with pulse generator 210 to cause pulse generator 210 to compose and issue the proper detection profile 240.

Computer 50, in the preferred embodiment, is a general purpose programmable computer including a display, I/O (keyboard, pointing device(s), voice recognition subsystems), a central processing unit, volatile and non-volatile memory, including fixed and portable media (e.g., floppy or zip disks), for storing sequences of instructions to operate in conjunction with the central processing unit and to control PAMURS instrument 200, and to analyze data from detector 230 as will be described further below. Additionally, computer 50 interacts in a well-known fashion with database 55. Computer 50 communicates with controller 40 and detector 230 in any of a number of ways, depending upon a particular application. In some cases, controller 40, computer 50, and database 55 may be integrated into a single device. In other cases, one or more components may be located remote from the other or others. In such cases, the components may communicate with each other through hard-wire connection including fiber optic, network or Internet connections, or through wireless communications channels.

Database 55 includes libraries of signature resonance frequencies for various macromolecules and foreign bodies (i.e., interferents and contaminants), and reactive resonance frequencies for those macromolecules. Either stored directly, or derived from the data stored in database 55, computer 50 establishes the desired detection profile 240 to be transmitted from pulse generator 210. Database 55 may be locally or remotely updated as new signature resonance frequencies or detection profiles are established and verified.

Transceiver 220 receives an emission profile 250 which is the frequency profile that results from interaction of detection profile 240 with sample S. Sample S, depending upon the macromolecule and foreign body composition, will interact with detection profile 240 to radiate emission profile 250. Transceiver 220 passes emission profile 250 on to detector 230 for detection and analysis, and is constructed dependent upon the nature of the re-radiated frequencies in the emission profile.

Detector 230, in the preferred embodiment, determines the existence and attenuation level of the radiation in T-wave absorption profile 250. In some instances, detector 230 checks only each T-wave base frequency included in detection profile 240. In other instances, it may additionally check for evidence of interaction of detection profile 240 and a foreign body between transceiver 220 and sample S by checking for the existence of frequencies in emission profile 250 indicating the presence of such foreign bodies.

Detector 230, in conjunction with computer 50, analyzes emission profile 250 and compares it to detection profile 240 and to data in database 55 to establish desired information about sample S. Depending upon the operational mode or the degree of specificity to which macromolecules in sample S are to be detected or identified, one or more iterations may be necessary.

III. Operation

A. Absorption Detection Mode

In operation, the preferred embodiment for PAMURS instrument 10 shown in FIG. 1 detects, identifies and/or disrupts selective macromolecules in sample S. In the example wherein an operator desires to determine whether sample S includes a specific macromolecule, the operator uses computer 50 to query database 55 to determine a specific detection profile 100. Detection profile 100 preferably includes three T-wave base frequencies which are uniquely resonant with the desired macromolecule.

Computer 50 issues control signals to controller 40 to initiate controller 40 in turn to cause T-wave generator 20 to compose and issue detection profile 100 towards sample S. When detection profile 100 reaches sample S, the set of T-waves in detection profile 100 will interact with various macromolecules, compounds and foreign bodies in sample S, the degree to which the interaction occurs is dependent upon the resonance frequencies of the various macromolecules, compounds and foreign bodies themselves.

When detection profile 100 is properly formed as set forth in this example, one of two conditions will exist for absorption profile 110. Either all of the incident radiation is absorbed, resulting in substantial attenuation of the entire set of T-waves or the absorption profile substantially matches the detection profile. The determinant for establishing which condition exists is dependent upon whether sample S includes the proper macromolecule in sufficient concentration relative to the strength of the appropriate T-waves. When sample S includes the macromolecule tested for, absorption profile 110 includes sufficiently attenuated signals at all three T-wave frequencies. When sample S does not include the macromolecule tested for, absorption profile 110 includes unattenuated signals at all three T-wave frequencies.

B. Remote Detection Mode

In operation, the preferred embodiment for PAMURS instrument 200 shown in FIG. 2 detects, identifies and/or disrupts selective macromolecules in sample S. In the example wherein an operator desires to determine whether sample S includes a specific macromolecule, the operator uses computer 50 to query database 55 to determine a specific detection profile 240. Detection profile 240 preferably includes three T-wave base frequencies which are uniquely resonant with the desired macromolecule and cause the specific macromolecule to re-radiate at one or more unique frequencies for a sufficient period of time to be detectable.

Computer 50 issues control signals to controller 40 to initiate controller 40 in turn to cause T-wave generator 210 to compose and issue detection profile 240 towards sample S. When detection profile 240 reaches sample S, the set of T-waves in detection profile 240 will interact with various macromolecules, compounds and foreign bodies in sample S, the degree to which the interaction occurs is dependent upon the resonance frequencies of the various macromolecules, compounds and foreign bodies themselves.

When detection profile 240 is properly formed as set forth in this example, one of two conditions will exist for emission profile 250. Either all of the incident radiation is absorbed by the specific macromolecule inducing it to re-radiate at the expected frequency or frequencies, resulting in substantial presence of these frequencies in the emission profile, or there is re-radiation at the expected frequency or frequencies due to the absence of the specific macromolecule. The determinant for establishing which condition exists is dependent upon whether sample S includes the proper macromolecule in sufficient concentration relative to the strength of the appropriate T-waves. When sample S includes the macromolecule tested for, emission profile 250 includes strong signals at all the expected re-radiation frequencies. When sample S does not include the macromolecule tested for, emission profile 110 does not include the expected signals at all relevant frequencies.

IV. Preferred Embodiments for Pulse Generators

The structure of the pulse generator is dependent upon the particular frequency or frequencies that are to be generated, with a structure for generation of pulses in the far infrared varying from a structure for generation of pulses in the deep ultraviolet. It is a goal of the following embodiments to provide a pulse signal (e.g., a T-wave pulse) having an interaction with a sample S that may be measured relatively free from uncertainties that a perceived signal attenuation was not due to random or system noise. The following are preferred embodiments for generation of non-sinusoid pulses suitable for use in various applications.

A. First Embodiment

Figure 3:
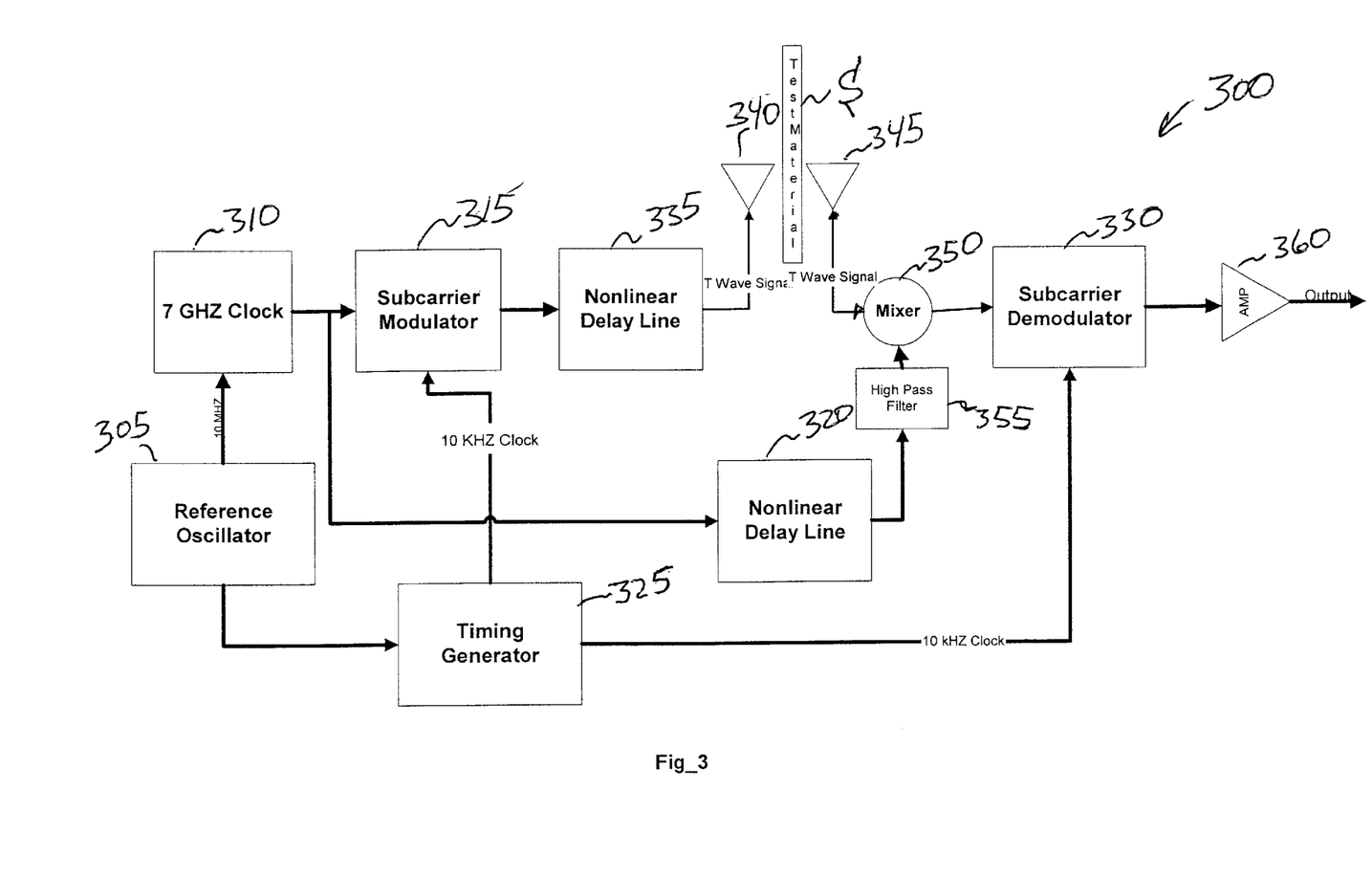
FIG. 3 is a block diagram of a preferred embodiment for a pulse generator, most applicable for the TeraHertz frequency range

FIG. 3 is a block diagram of a preferred embodiment for a pulse generator and PAMURS instrument 300, most applicable for the TeraHertz frequency range. PAMURS instrument 300 includes a reference oscillator 305 that provides a ten megaHertz reference clock signal to a seven gigaHertz clock 310 generator. Output of clock generator 310 is provided to a subcarrier modulator 315 and to a non-linear delay line 320. A timing generator 325 provides a ten kiloHertz clock signal to subcarrier modulator 315 and to a subcarrier demodulator 330. Subcarrier modulator 315 provides an output to a nonlinear delay line 335. An output of nonlinear delay line 335 is communicated to a T-wave transmitting antenna 340.

A T-wave receiving antenna 345 receives the transmitted pulses after they have passed through sample S as described above. The signal from T-wave receiver antenna 345 is provided to a mixer 350, which mixes the received signal with an output of a high pass filter 355 that filters an output of nonlinear delay line 320. An output of mixer 350 is provided to subcarrier demodulator 330. An output of subcarrier demodulator 330 is provided to an amplifier 360. An output of amplifier 360 provides a signal which indicates the degree to which sample S has attenuated the input signal free with reduced inaccuracies due to noise.

Further details of the construction, and the operation, of a subcarrier modulator and a subcarrier modulator are disclosed in U.S. Pat. No. 5,677,927, entitled and U.S. Pat. No. 5,995,534, each entitled "Ultrawide-Band Communication System and Method" and hereby expressly incorporated by reference for all purposes. In this preferred embodiment, the modulation and demodulation of the output of the sinusoidal seven gigaHertz signal, among other things, allows for the filtering of 1/f noise and drift found in the receiver input.

The output of nonlinear delay line 320 is a saw-toothed wave form, which when transmitted by T-wave antenna 340 becomes a very sharp differentiated waveform that is a pulse shaped monocycle wave. The purpose of the delay lines (e.g., after the sub carrier modulation) is to create the sharp trailing edges (e.g., changes the waveform to create "saw tooth" type of wave form). This waveform has a trailing edge in the order of 140 Pico seconds. The transmitter antenna differentiates this waveform to cause the transmission of the THz pulse. The pulse is received by the receiving antenna and enters the mixer. A second non-linear delay line is fed into the mixer (through a high pass filter) from the output of the 7 GHZ clock. This creates the second "saw tooth" wave form with the sharp trailing edges enabling the subcarrier demodulation after being mixed. The timing generator which is output from the reference oscillator keeps synchronization. The output of the subcarrier demodulation is output via an amplifier. This is where the macro-molecule determination processing occurs.

Further details regarding the nonlinear delay line are available from "Delta-doped Schottky Diode Nonlinear Transmission Lines for 480-fs, 3.5-V Transients" Applied Physics Letter 65, No. 7, 881–883 (August 1994), and further details regarding the mixer are available from "GaAs-Membrane-Diode Mixer for Operations at 2.5 THz" Electronics Tech Briefs Magazine, ETB029906, February 1999, or from Technology Reporting Officer, JPL, MS 122–116, 4800 Oak Grove Drive, Pasadena, Calif. 91109, both hereby expressly incorporated by reference for all purposes.

B. Second Embodiment

Figure 4:
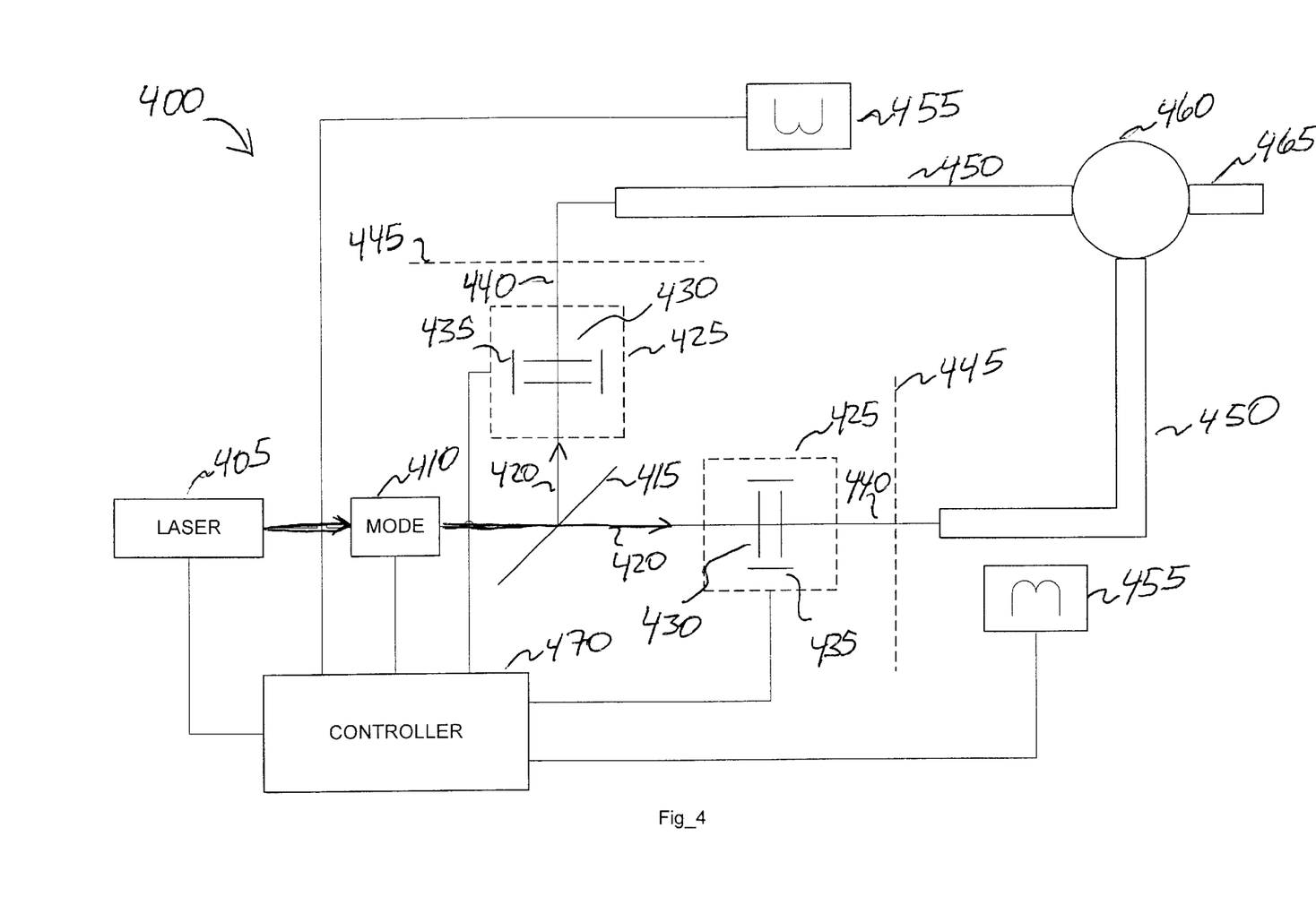
FIG. 4 is a block diagram of a preferred embodiment for a pulse generator.

FIG. 4 is a block diagram of a preferred embodiment for a pulse generator 400. Pulse generator 400 includes a laser 405, with laser 405 selected to penetrate the medium through which the signal is to be aimed. For example, the red lasers used in LIDAR mapping could be used over land, or blue-green lasers normally used for bathymetric measurements could be used in high water environments. A laser mode control 410 selects the desired mode for the emitted laser beam and laser 405 is aimed at one or more beam splitters 415 to create an appropriate number of beams 420 needed to create an output pulse. Each beam 420 is fed into a photonic gate 425. Photonic gates 425 include a Fabry-Perot etalon 430 that is filled with a material that, when subjected to a varying magnetic field created by electromagnet 435, will change the internal path length of etalon 430 at the incident frequency. The change in path length changes the power allowed through the etalon, from 0 to 1 times the incident beam continuously. A beam 440, emitted from photonic gate 425, passes through a magnetic shield 445 into a fiber optic path 450 with a magnetic half coil 455 oriented to generate a magnetic field through fiber optic path 450. The magnetic field created by half-coil 455 phase shifts beam 440 in fiber optic path 450. A combiner 460 receives the beams 440 and combines them to produce an output pulse 465. A controller coupled to laser 405, mode control 410, the photonic gates 425 and half coils 455 controls the operation of pulse generator 400 as follows.

The laser has a very short base, therefore it will pass any interferents and contaminants, therefore what needs to be done is control of the frequency and pulse characteristics. As the beam is split into beams 420, controller 470 sets both photonic gates 425 at one. However, controller 470 activates a half coil 455 to produce a magnetic field on one fiber optic path 450 phase that shifts a beam 420 through that path such that it is exactly out of phase with the other beam. In this initial condition, combiner 460 outputs zero power.

To emit the lead pulse (e.g., T-wave), controller 470 sends a signal to both photonic gates 425 to go to zero. However, the distance through the second path and second photonic gate is one wavelength longer than the path. Therefore, the first photonic gate closes, one pulse is emitted, and the second photonic gate closes. When the time for the next pulse is to be emitted, the controller sends a signal to both photonic gates that both gates are to go to one. The first photonic gate opens, one T-wave is emitted, and the second gate opens out of phase with the first one and the power goes to zero again. To enable greater flexibility using controller 470, the path length of the second photonic gate is also controlled by a magnetic field also, using the same material that is used in the etalons. To put out the three unique signals, three of these circuits need to be constructed.

C. Third Embodiment

Figure 5:
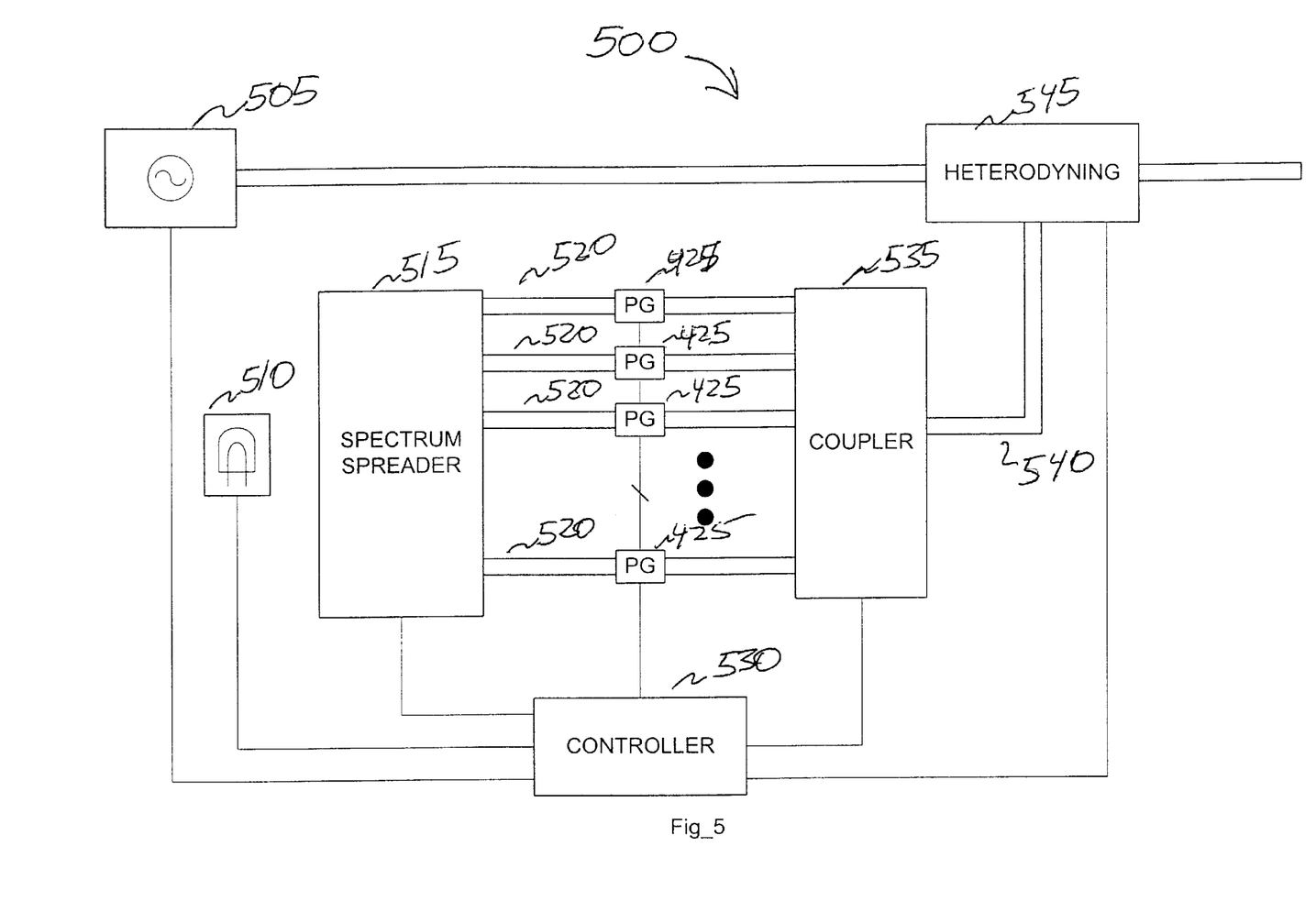
FIG. 5 is a block diagram of a preferred embodiment for a pulse generator applicable to a different frequency range.

FIG. 5 is a block diagram of a preferred embodiment for a pulse generator 500 which may be used in the ultraviolet range. Some of the signals are best observed at ultraviolet or other ranges. However, ultraviolet and some of these other ranges do not penetrate samples or atmosphere well. In the preferred embodiment, to use the ultraviolet and other higher frequencies, pulse generator 500 heterodynes the desired signal onto a microwave signal provided from a microwave source 505. A preferred embodiment of pulse generator 500 uses a broadband source 510 of ultraviolet light. Mercury lamps are one potential source for broadband source 510, although other sources might also be used especially for other ranges of interest. A spectrum spreader 515 receives the radiation from broadband source 510 to spread the input spectrum to the point that a series of fiber optic threads 520 laid out side by side in a straight path are able to absorb a bandwidth within the range needed for the unique identification of the target molecule. Along each fiberoptic thread 520, a photonic gate 425 is placed. Each photonic gate 425 is set for the unique identifying signal, and responds to control signals from a controller 530 such that one photonic gate 425, for a specific frequency, is open with all other closed. A coupler 535 takes the outputs from the fiberoptic threads 520 and combines them all into a single path 540. A heterodyning circuit 545 heterdynes the selected signal on path 540 with an output of microwave source 505. The output is radiated as the desired pulse. Then the detector circuit watches for absorption, or re-radiation in different bands as described above. The strength of the signal after its interaction with the sample is correlated with the concentration of the target molecules.

As a variation of this embodiment, it is possible to provide individually tuned monochromatic radiation sources. For example, a company provides for blue laser diodes that may be tuned during the manufacturing process to precisely desired frequencies. In some applications, it may be desirable to replace the broadband source and spectrum spreader with an array of precisely tuned laser diodes directly coupled to the fiberoptic threads. The Nichia Chemical Industries Limited company having an address in Tokushima, Japan advertises the manufacture, production and use of these diodes and would be one potential source.

V. Conclusion

In conclusion, the preferred embodiments of the PAM-URS instruments described herein offer superior performance and reliability over prior art techniques of macromolecule detection, identification and disruption. While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for detecting the presence of a macromolecule having one or more resonant frequencies in the electromagnetic spectrum, comprising:

a pulse generator capable of generating RF waves having a frequency in the range of $1 \times 10^{12}$ Hz to about $3 \times 10^{16}$ Hz for generating a detection profile having a detection set of incident RF waves and applying said detection profile to a sample including the macromolecule, at least one incident RF wave having a center frequency substantially centered on one of the resonant frequencies of the macromolecule;

a detector for receiving the detection profile after said application of said detection profile to said sample;

an analyzer, coupled to said detector, for determining an incident RF wave absorption profile by identifying which incident waves of said set of incident waves have been wholly or partially absorbed by the sample and to subsequently identify the macromolecule by use of the absorption profile.

2. The detection system of claim 1 wherein said detection profile comprises T-waves of at least two different resonant frequencies of said macromolecule.

3. The detection system of claim 1 wherein said incident waves have center frequencies substantially in the far infrared range of the electromagnetic spectrum.

4. The detection system of claim 3 wherein said sample includes one or more interferents each having absorption characteristics for T-waves collectively defining a set of interferent frequencies in the far infrared range of the electromagnetic spectrum for said interferents and wherein said detection profile excludes T-waves having center frequencies substantially equal to said set of interferent frequencies.

5. A system for detecting the presence of a macromolecule having one or more resonant frequencies in the electromagnetic spectrum, comprising:

a T-wave generator for generating a detection profile having a detection set of at least one T-wave and applying said detection profile to a sample including the macromolecule, the at least one T-wave having a center frequency substantially centered on one of the resonant frequencies of the macromolecule, said resonant frequency inducing said macromolecule to reradiate an emission profile including a set of emission frequencies different from frequencies of said set of T-waves;

a detector for receiving the emission profile after said application of said detection profile to said sample;

an analyzer, coupled to said detector, for determining a T-wave absorption profile by identifying which T-waves of said set of T-waves have been wholly or partially absorbed by the sample as derived from said emission profile and to subsequently identify the macromolecule.

6. The detection system of claim 5 wherein said detection profile includes a plurality of T-waves, including those of at least two different resonant frequencies of said macromolecule.

7. The detection system of claim 5 wherein said T-waves have center frequencies substantially in the far infrared range of the electromagnetic spectrum.

8. The detection system of claim 7 wherein said sample includes one or more interferents each having absorption characteristics for a T-waves collectively defining a set of interferent frequencies in the far infrared range of the electromagnetic spectrum for said interferents and wherein said detection profile excludes T-waves having center frequencies substantially equal to said set of interferent frequencies.

9. A method for detecting the presence of a macromolecule having one or more resonant frequencies in the far infrared region of the electromagnetic spectrum, comprising the steps of:

generating a detection profile having a detection set of T-waves wherein at least one T-wave has a center frequency substantially centered on one of the resonant frequencies of the macromolecule;

applying said detection profile to a sample including the macromolecule; thereafter receiving the detection profile after said application of said detection profile to said sample;

determining a T-wave absorption profile by identifying which T-waves of said set of T-waves have been wholly or partially absorbed by the sample; and identifying the macromolecule by use of the absorption profile.

10. A method for detecting the presence of a macromolecule having one or more resonant frequencies in the far infrared region of the electromagnetic spectrum, comprising the steps of:

generating a detection profile having a detection set of T-waves wherein at least one T-wave has a center frequency substantially centered on one of the resonant frequencies of the macromolecule, said resonant frequency inducing said macromolecule to reradiate an emission profile including a set of emission frequencies different from frequencies of said set of T-waves;

applying said detection profile to a sample including the macromolecule;

receiving the emission profile after said application of said detection profile to said sample;

determining a T-wave absorption profile by identifying which T-waves of said set of T-waves have been wholly or partially absorbed by the sample as derived from said emission profile; and thereafter identifying the macromolecule based upon the absorption profile.

11. A method for screening a sample to determine whether it contains a macromolecule of interest, comprising the steps of:

generating a detection profile having a detection set of T-waves wherein said detection profile includes at least one T-wave having a center frequency substantially centered on at least one resonant frequency of one of a set of macromolecules, said resonant frequency inducing at least one macromolecule to reradiate an emission profile including a set of emission frequencies different from frequencies of said set of T-waves;

applying said detection profile to a sample;

receiving any emission profile from the sample after said application of said detection profile to said sample;

determining a T-wave absorption profile by identifying which T-waves of said set of T-waves have been wholly or partially absorbed by the sample as derived from said emission profile; and thereafter identifying a presence of one of said set of macromolecules based upon the absorption profile when at least one T-wave has induced an emission profile from said sample.

12. A method for fragmenting a macromolecule having one or more resonant frequencies in the far infrared region of the electromagnetic spectrum, comprising the steps of:

generating a fragmenting profile having a fragmentation set of T-waves wherein at least one T-wave has a center frequency substantially centered on one of the resonant frequencies of the macromolecule; and applying said fragmentation profile to a sample including the macromolecule for sufficient duration and at sufficient power to fragment said macromolecule.

13. A real-time method for detecting and identifying macromolecules, comprising the steps of:

searching for macromolecules in a broadband search mode using a resonance spectrometer capable of generating at least one electromagnetic emission within the range of from $1 \times 10^{12}$ Hertz and $3 \times 10^{16}$ Hertz and obtaining a first set of search results;

generically identifying one or more types of macromolecule present from the broadband search results by searching a database of absorption or emissions spectra;

searching for one or more types of macromolecules in a narrowband mode and obtaining a second set of search results; and specifically identifying the one or more types of macromolecules present by searching the second set of search results against the database of absorption or emission spectra.

14. A method as claimed in claim 13, wherein the broadband search is a notch filter search employing a selected group of frequencies.

15. A method as claimed in claim 13, further comprising the step of updating the database of absorption or emissions spectra from the search results.

16. A method as claimed in claim 13, further comprising the step of:

disrupting a selected macromolecule by transmitting T-waves from a pulse generator.

\* \* \* \* \*